US008685066B2

(12) United States Patent
Stad et al.

(10) Patent No.: US 8,685,066 B2
(45) Date of Patent: Apr. 1, 2014

(54) DEVICES AND METHODS FOR POSITIONING A SPINAL FIXATION ELEMENT

(71) Applicant: DePuy Synthes, Raynham, MA (US)

(72) Inventors: Shawn D. Stad, Fall River, MA (US); David G. Anderson, Philadelphia, PA (US); Tony Tannoury, Andover, MA (US); Paul G. Beaudoin, Derry, NH (US); Sara Dziedzic, Dorchester, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/625,034

(22) Filed: Sep. 24, 2012

(65) Prior Publication Data

US 2013/0018423 A1    Jan. 17, 2013

Related U.S. Application Data

(63) Continuation of application No. 11/861,551, filed on Sep. 26, 2007, now abandoned.

(51) Int. Cl.
  *A61B 17/88*    (2006.01)
(52) U.S. Cl.
  USPC ........................................ 606/279; 606/86 A
(58) Field of Classification Search
  USPC ................. 606/246–279, 103, 86 A, 86 R, 99
  See application file for complete search history.

(56) References Cited

U.S. PATENT DOCUMENTS

| | | | |
|---|---|---|---|
| 6,530,929 B1 | 3/2003 | Justis et al. | |
| 7,008,422 B2* | 3/2006 | Foley et al. | 623/17.16 |
| 7,011,660 B2* | 3/2006 | Sherman et al. | 606/86 A |
| 7,179,261 B2 | 2/2007 | Sicvol et al. | |
| 7,250,052 B2* | 7/2007 | Landry et al. | 606/86 A |
| 7,497,869 B2* | 3/2009 | Justis | 606/279 |
| 7,520,879 B2* | 4/2009 | Justis et al. | 606/86 A |
| 7,527,638 B2* | 5/2009 | Anderson et al. | 606/279 |
| 7,547,318 B2* | 6/2009 | Birkmeyer et al. | 606/279 |
| 8,262,662 B2* | 9/2012 | Beardsley et al. | 606/86 A |
| 2003/0229347 A1* | 12/2003 | Sherman et al. | 606/61 |
| 2004/0039384 A1 | 2/2004 | Boehm et al. | |
| 2005/0065517 A1* | 3/2005 | Chin | 606/61 |
| 2005/0070917 A1* | 3/2005 | Justis | 606/104 |
| 2005/0090824 A1* | 4/2005 | Shluzas et al. | 606/61 |
| 2005/0131419 A1 | 6/2005 | McCord et al. | |
| 2005/0131420 A1 | 6/2005 | Techiera et al. | |
| 2005/0131421 A1* | 6/2005 | Anderson et al. | 606/99 |

(Continued)

FOREIGN PATENT DOCUMENTS

WO    2007087516    8/2007

*Primary Examiner* — Eduardo C Robert
*Assistant Examiner* — Lynnsy Schneider
(74) *Attorney, Agent, or Firm* — Nutter McClennen & Fish LLP (57) ABSTRACT

Methods for delivering a spinal fixation element to a surgical site are provided herein. More specifically, the method includes delivering a plurality of percutaneous access devices to a corresponding number of spinal locations, inserting a spinal fixation element through tissue, and manipulating the element through opposed sidewall openings formed in each access device. In an exemplary embodiment, the method can be optimized for position of large-scale fixation elements (e.g., greater than about 95 mm in length). In addition, a manipulation instrument configured to position such spinal fixation elements is also provided herein.

19 Claims, 11 Drawing Sheets

(56) References Cited

U.S. PATENT DOCUMENTS

| | | |
|---|---|---|
| 2005/0131422 A1 | 6/2005 | Anderson et al. |
| 2005/0154389 A1* | 7/2005 | Selover et al. ............... 606/61 |
| 2005/0171540 A1* | 8/2005 | Lim et al. .................... 606/61 |
| 2005/0192579 A1* | 9/2005 | Jackson ....................... 606/72 |
| 2005/0192589 A1* | 9/2005 | Raymond et al. ............ 606/99 |
| 2005/0215999 A1* | 9/2005 | Birkmeyer et al. ........... 606/61 |
| 2005/0251139 A1* | 11/2005 | Roh .............................. 606/61 |
| 2005/0277934 A1* | 12/2005 | Vardiman ..................... 606/61 |
| 2006/0036255 A1* | 2/2006 | Pond et al. .................... 606/86 |
| 2006/0111713 A1* | 5/2006 | Jackson ....................... 606/61 |
| 2006/0167454 A1* | 7/2006 | Ludwig et al. ............... 606/61 |
| 2006/0184178 A1* | 8/2006 | Jackson ....................... 606/99 |
| 2006/0247630 A1* | 11/2006 | Iott et al. ...................... 606/61 |
| 2007/0016194 A1* | 1/2007 | Shaolian et al. .............. 606/61 |
| 2007/0073294 A1* | 3/2007 | Chin et al. .................... 606/61 |
| 2007/0078460 A1* | 4/2007 | Frigg et al. ................... 606/61 |
| 2007/0191840 A1* | 8/2007 | Pond et al. .................... 606/61 |
| 2007/0213714 A1* | 9/2007 | Justis ............................ 606/61 |
| 2007/0233079 A1* | 10/2007 | Fallin et al. .................. 606/61 |
| 2007/0270819 A1* | 11/2007 | Justis et al. ................... 606/61 |
| 2007/0270842 A1* | 11/2007 | Bankoski et al. ............. 606/61 |
| 2007/0288002 A1* | 12/2007 | Carls et al. ................... 606/61 |
| 2008/0009864 A1* | 1/2008 | Forton et al. ................. 606/61 |
| 2008/0045956 A1* | 2/2008 | Songer et al. ................. 606/61 |
| 2008/0051787 A1* | 2/2008 | Remington et al. ........... 606/61 |
| 2008/0077138 A1* | 3/2008 | Cohen et al. ................. 606/61 |
| 2008/0125788 A1* | 5/2008 | Cohen et al. ................ 606/104 |
| 2008/0269805 A1* | 10/2008 | Dekutoski et al. .......... 606/279 |
| 2008/0312703 A1* | 12/2008 | Hestad et al. ............. 606/86 A |
| 2009/0062857 A1* | 3/2009 | Ramsay et al. ............. 606/246 |
| 2009/0062859 A1* | 3/2009 | Mahoney et al. ........... 606/278 |
| 2009/0082811 A1 | 3/2009 | Stad et al. |

* cited by examiner

DEVICES AND METHODS FOR POSITIONING A SPINAL FIXATION ELEMENT

CROSS REFERENCE TO RELATED APPLICATIONS

The present application is a continuation of U.S. patent application Ser. No. 11/861,551 filed on Sep. 26, 2007 and entitled "Devices and Methods for Positioning a Spinal Fixation Element." This reference is hereby incorporated by reference in its entirety.

FIELD OF USE

Methods and devices are provided herein for use in spinal surgery, and in particular to methods and devices for positioning a spinal fixation element.

BACKGROUND

For a number of reasons, spinal fixation devices are used in orthopedic surgery to align and/or fix a desired relationship between vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive devices and methods for implanting spinal fixation devices. One such method, for example, is disclosed in U.S. Pat. No. 6,530,929 of Justis et al. and it utilizes two percutaneous access devices for implanting an anchoring device, such as a spinal screw, into adjacent vertebrae. A spinal rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle. Moreover, the use of three separate access sites can undesirably lengthen the surgical procedure, and increase patient trauma and recovery time.

In general, current minimally invasive procedures have been limited to the use of relatively short spinal fixation elements (e.g., less than about 95 mm) thereby limiting the availability of minimally invasive surgery in some spinal fusion procedures. For example, a 95 mm spinal fixation element is typically limited to a maximum of a three level fusion. Thus, there remains a need for devices and methods capable of providing increased treatment options.

SUMMARY

Methods and instruments for delivering a spinal fixation element to a surgical site are provided herein. More specifically, the various embodiments enable surgeons to perform high level spinal fusions (traversing three vertebra, four vertebra, five vertebra, etc.) by means of minimally invasive surgical procedures. Thus, the methods and instruments can be configured to allow for positioning of a large spinal fixation element (e.g., greater than about 95 mm in length) within a plurality of spinal anchors engaged to various spinal locations. Additionally, the disclosed surgical procedures can be configured to minimize the number of incisions thereby minimizing any tissue damage (and resulting patient discomfort) associated with the procedure.

Various aspects of the method are provided herein. For example, in one aspect, the method includes engaging a plurality of percutaneous access devices to a corresponding number of spinal locations. Each access device can be delivered to the respective spinal location via a respective incisions such that, for example, at least a first access device is delivered via a first incision. Thus, the method can be configured to limit the number of required incisions to the number of percutaneous access devices being utilized in any given procedure. Each percutaneous access device can include a distal end disposed adjacent to a spinal anchor and a proximal end positioned outside a patient's body. The method next includes delivering a distal portion of a spinal fixation element through the first incision, manipulating the distal portion of the spinal fixation element through opposed sidewall openings of the first percutaneous access device, and guiding the spinal fixation element through opposed sidewall openings of each percutaneous access device. As such, the spinal fixation element can be delivered through the percutaneous access devices from the outside of the first device thereby eliminating the need to pass the fixation element longitudinally along an inner lumen of the access device. The method can further include placing the spinal fixation element within the plurality of spinal anchors such that at least a portion of the spinal fixation element resides within each of the plurality of spinal anchors, and releasing the spinal fixation element from the manipulation instrument following the placing step.

As known to those of skill in the art, the spinal fixation element can include any such element capable of providing the desired spinal fusion. For example, in an exemplary embodiment, the spinal fixation element is a fixation rod. While the spinal fixation element can be of any desired length, in exemplary embodiments, the length of the spinal fixation element is greater than about 95 mm, greater than about 100 mm, etc. In general, the length of the spinal fixation element is selected so as to achieve the desired level of spinal fusion (e.g., across three vertebrae, across four vertebra, across five vertebra, etc.).

As indicated, the method includes delivering a plurality of percutaneous access devices to a corresponding number of spinal locations. The number of percutaneous access devices can vary depending on the procedure. For example, the method can utilize two such devices, three such devices, four such devices, or more than four such devices. Thus, the method can allow for a large number of such devices to be utilized thereby allowing fusions of greater levels and further allowing fusions spanning across various regions of the spine.

The percutaneous access devices can be configured in various manners. Generally, the devices include a distal end configured to releasably engage a spinal anchor, and a proximal end positioned outside of a patient's body. In an exemplary embodiment, the proximal end of at least one (or all) of the percutaneous access devices can be closed because the spinal fixation element is not being delivered axially along an inner lumen of the device but rather being delivered laterally through opposed sidewall openings. As will be discussed, the use of a percutaneous access device having a closed proximal end facilitates various downstream steps.

The spinal fixation element can be delivered and/or manipulated through the opposed sidewall openings of the various percutaneous access devices in various manners. For example, in one aspect, the method can include releasably engaging a proximal portion of the spinal fixation element to a distal portion of a manipulation instrument. As discussed below, the manipulation instrument can be configured in various manners so as to facilitate the delivery and positioning of a relatively large-scale spinal fixation element at the surgical site. The method can further include disengaging the spinal fixation element from the manipulation instrument after the spinal fixation element passes through the opposed sidewall openings of each percutaneous access device. In one such embodiment, the releasably engaging step of the method can include disposing the proximal end of the spinal fixation element within an opening formed in a distal portion of the manipulation instrument, and securing the spinal fixation element to the manipulation instrument by engaging a distal end of an engagement element to a notch formed in a proximal portion of the spinal fixation element wherein the engagement element is disposed in a distal portion of the manipulation instrument. Also, the releasing step of the method can include applying an actuation force to an actuator wherein the actuation force can disengage the distal end of the engagement element from the notch formed in the proximal portion of the spinal fixation element.

In another aspect, a minimally invasive method for delivering a spinal fixation element to a surgical site is provided which includes inserting a plurality of access devices into a body through a percutaneous incision for each access device such that a proximal end of each access device is positioned outside the body and a distal end engages a spinal anchor disposed in a vertebra. Next, the method can include inserting a spinal fixation element through one of the percutaneous incisions for one of the access devices such that a distal portion of the spinal fixation element is positioned adjacent an outer portion of a first percutaneous access device. Further, the method can include manipulating the spinal fixation element such that the spinal fixation element passes through the opposed sidewall openings of each percutaneous access device. Once the spinal fixation element has been positioned through the opposed sidewall openings of each percutaneous access device, the method can further include placing the spinal fixation element in the plurality of spinal anchors such that at least a portion of the spinal fixation element resides within each bone anchor, and disengaging the spinal fixation element from the manipulation instrument following the placing step.

In another aspect, a method for delivering a spinal fixation element to a surgical site is provided which includes engaging a plurality of percutaneous access devices to a corresponding number of spinal locations with each access device being delivered to the respective spinal location via a respective incision such that at least a first access device is delivered via a first incision wherein each percutaneous access device can include a distal end disposed adjacent to a spinal anchor and a proximal end positioned outside a patient's body. The method can also include releasably engaging a proximal portion of a spinal fixation element to a distal portion of a manipulation instrument wherein the manipulation instrument includes a handle portion coupled to an elongate shaft via an offset. Further, the method can include delivering a distal portion of the spinal fixation element through the first incision, and manipulating the distal portion of the spinal fixation element through opposed sidewall openings of the first percutaneous access device. The method can also include guiding the distal portion of the spinal fixation element through opposed side wall openings of each percutaneous access device, and placing the spinal fixation element within the plurality of spinal anchors such that at least a portion of the spinal fixation element resides within the spinal anchors. Further, the method can also include releasing the spinal fixation element from the manipulation instrument following the above placing step.

In addition to the various aspects of the method provided above, an instrument for releasably engaging a spinal fixation element and positioning the element percutaneously into a spinal anchor is provided herein. In one such aspect, the instrument can include a handle having a proximal end and a distal end. The instrument can also include an offset having a proximal end and a distal end wherein the proximal end of the offset is coupled to the distal end of the handle and the distal end of the offset can extend into an elongate shaft. Further, the instrument can includes an opening formed in the distal end of the elongate shaft wherein the opening is configured to receive and releasably engage a proximal end of a spinal fixation element. Optionally, the distal portion of the elongate shaft can be configured to prevent passage of the shaft within a sidewall opening of a percutaneous access device attached to a spinal anchor.

The instrument can include various other components and/or features capable of facilitating placement and positioning of a spinal fixation element. For example, in one embodiment, the instrument can include an actuator coupled to the shaft wherein the actuator is configured to release an engaged spinal fixation element from the distal end of the device. Additionally, the instrument can include a distal portion of the elongate shaft which is angled relative to a proximal portion of the elongate shaft. As will be describe below, such an alignment can facilitate proper positioning of the fixation element within the bone anchors.

In another aspect, the device for releasably engaging a spinal fixation element and positioning the instrument can include a handle having a proximal end and a distal end wherein the distal end of the handle is coupled to an elongate shaft by an offset. Further, a distal end of the elongate shaft can include an opening which is configured to receive a proximal end of a spinal fixation element. The distal end of the instrument can also being configured to prevent passage of the manipulation instrument through a side-wall opening of a percutaneous access device. The instrument can also include an actuator coupled to the distal shaft of the instrument wherein the actuator can be in communication with an engagement element disposed within an inner lumen of the elongate shaft and being capable of moving the engagement element into and out of contact with a portion of the spinal fixation element disposed within the opening of the elongate shaft thereby retaining or releasing the spinal fixation element from the device upon actuation.

These and other aspects of the presently disclosed methods and devices are described in detail below.

BRIEF DESCRIPTION OF THE DRAWINGS

The various embodiments of the presently disclosed methods and devices will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the presently disclosed methods and devices.

Methods and devices for positioning a spinal fixation element at a surgical site are provided herein. In general, these methods and devices facilitate minimally invasive spinal fusion procedures that can span multiple levels of the spine (e.g., three levels or more) while minimizing any associated tissue damage. For instance, the method can include delivering a plurality of percutaneous access devices to various spinal locations via a corresponding number of incisions (e.g., four percutaneous access devices would require four incisions). Next, a spinal fixation element (e.g., a rigid rod, a polymer rod, a dynamic element, etc.) can be delivered through tissue via one of the existing incisions such that, for example, the spinal fixation element can be positioned adjacent an outer portion of a first percutaneous access device and delivered through the first incision into the patient. Once so positioned, the fixation element can be manipulated (e.g., via a manipulation instrument) so as to pass laterally through opposed sidewall openings of the first percutaneous access device and subsequently through the remainder of the access devices via similarly positioned opposed sidewall openings of each access device. Thus, the fixation element passes from the outside of the first percutaneous access device and transversely through the remainder of the devices. As will be discussed, such a delivery trajectory eliminates the need to introduce the fixation element axially through a proximal opening of the first percutaneous access device as such delivery and subsequent manipulation typically is difficult, if not impossible, when utilizing a fixation element having a length of greater than about 95 mm.

Figure 1A:
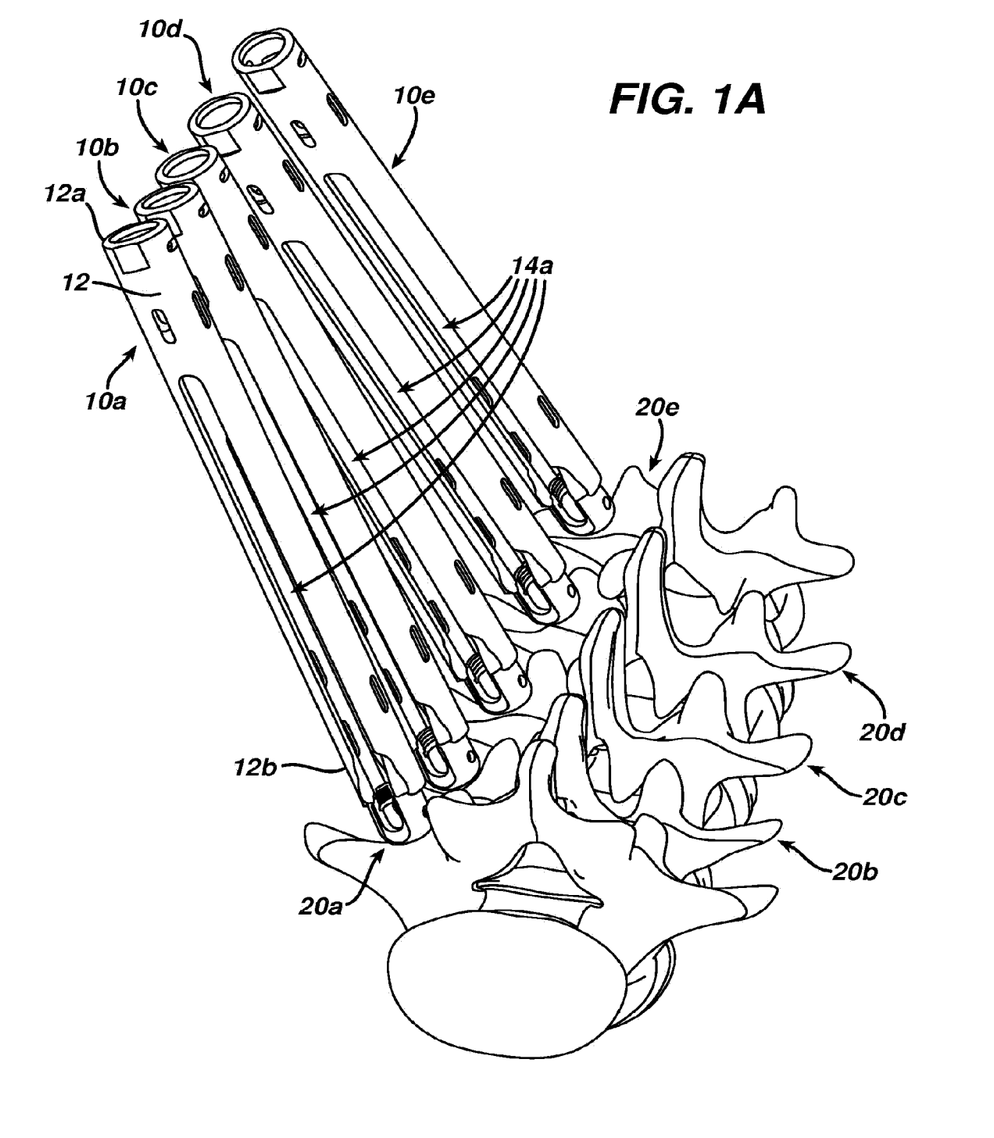
FIG. 1A is a representation of a plurality of percutaneous access devices engaged to a corresponding number of spinal locations.
Figure 1B:
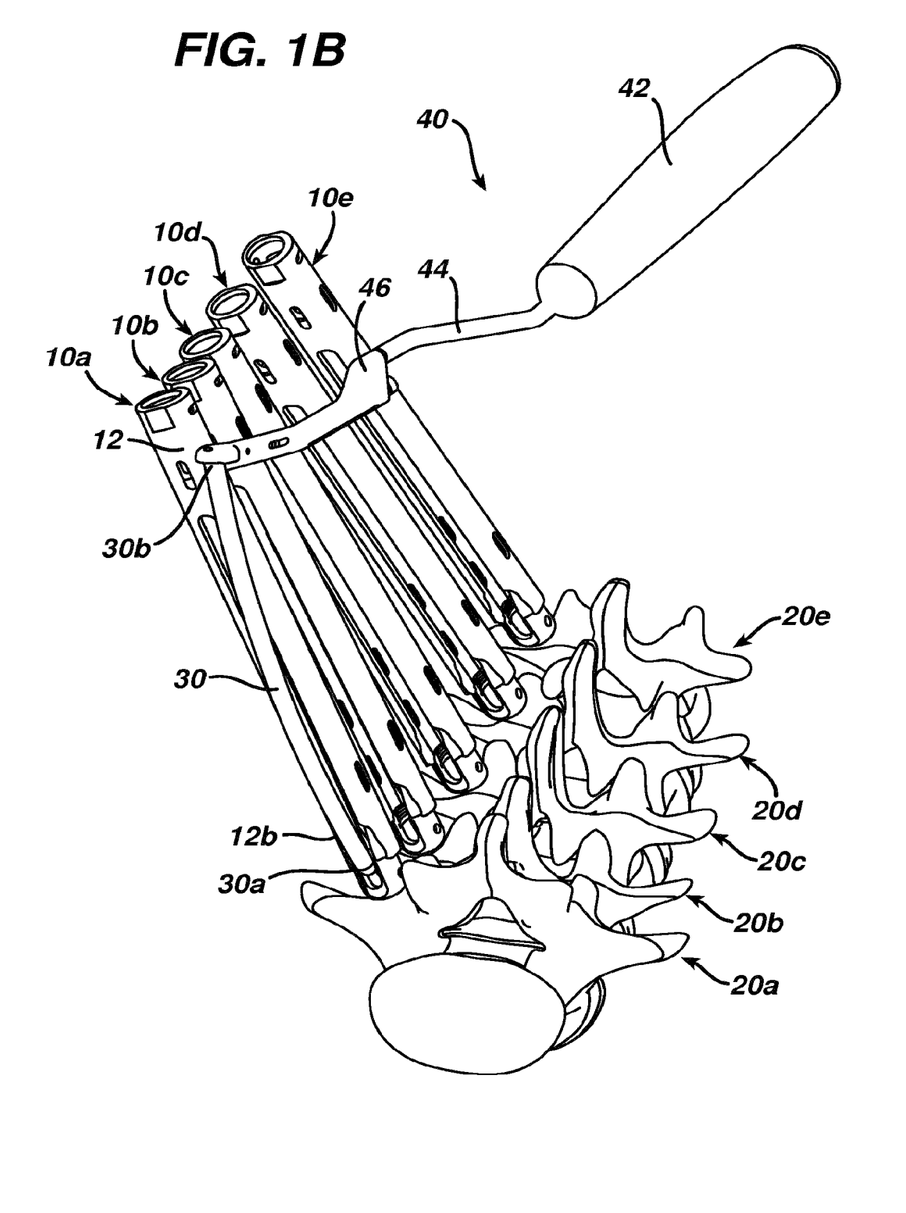
FIG. 1B is a representation of a spinal fixation element being delivered to a surgical site wherein the element is external and adjacent to a first percutaneous access device of the plurality of such devices shown in FIG. 1A.
Figure 1C:
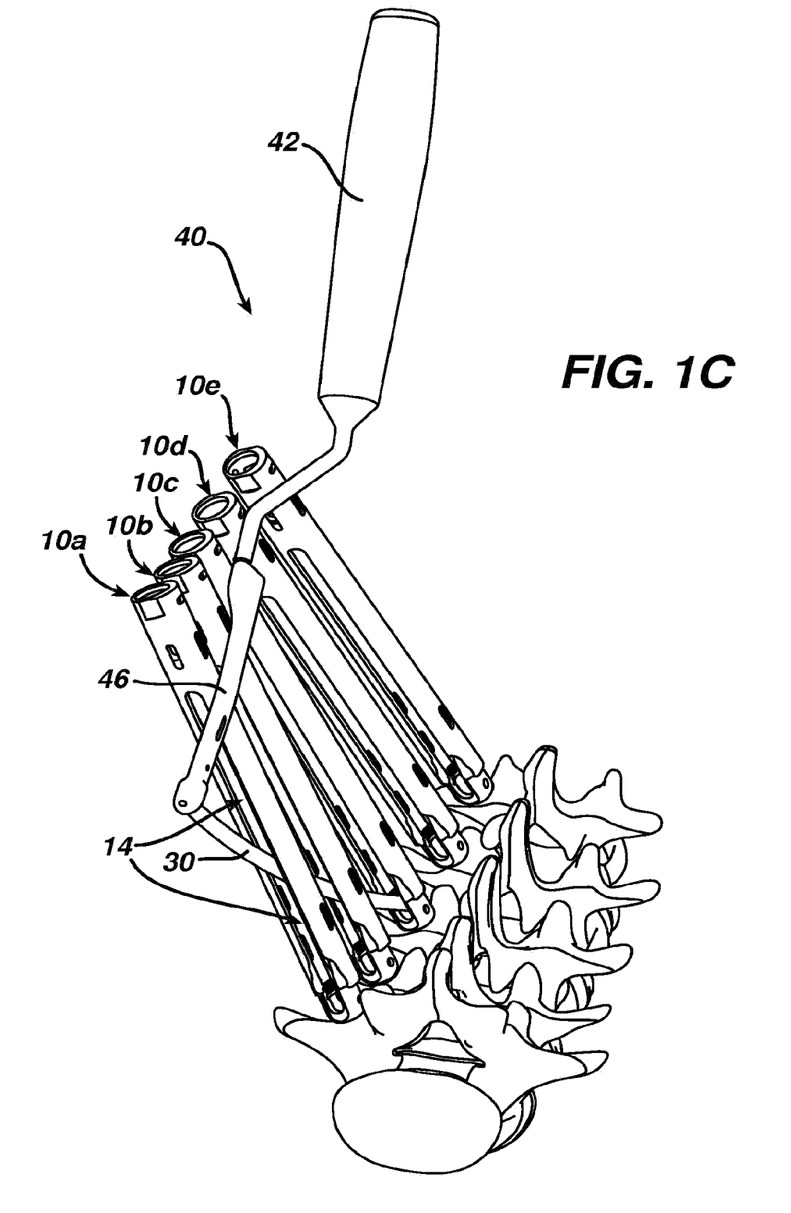
FIG. 1C is a representation of the spinal fixation element of FIG. 1B being laterally passed through the opposed sidewall openings of several of the percutaneous access devices of FIG. 1A.
Figure 1D:
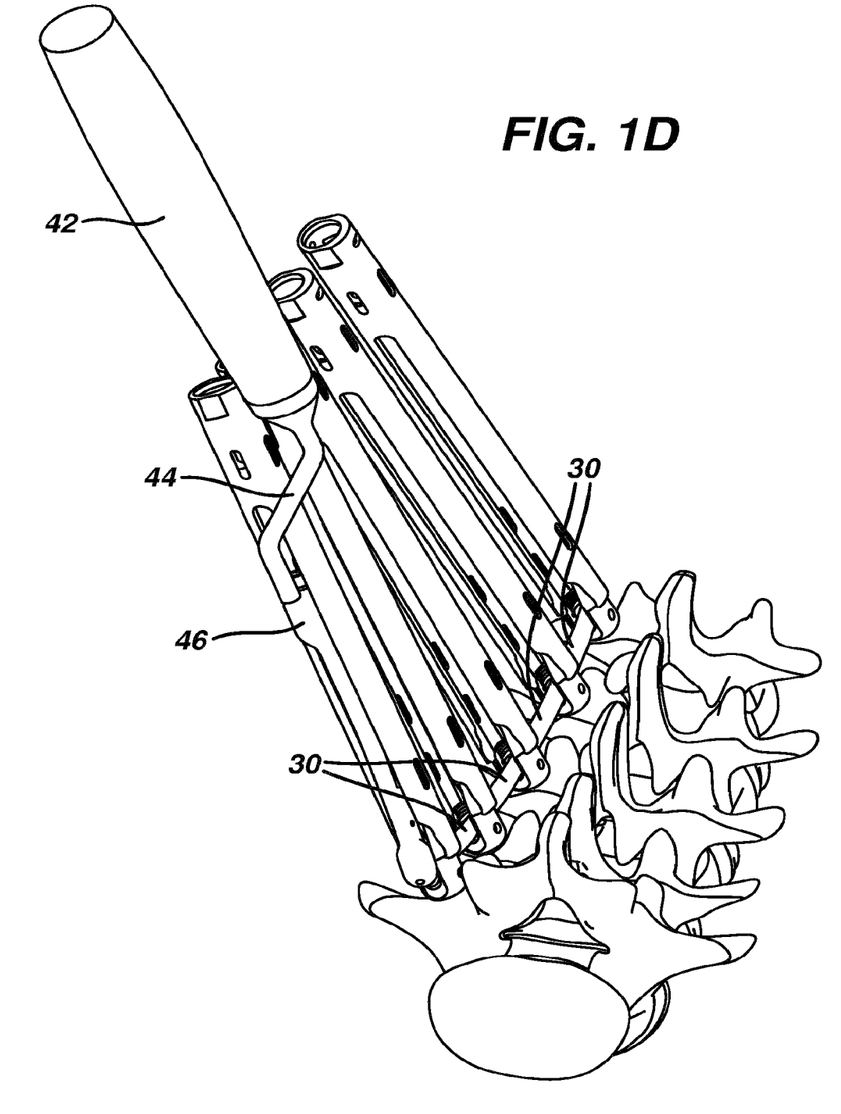
FIG. 1D is a representation of the spinal fixation element of FIG. 1B being positioned through the opposed sidewall openings of each percutaneous access devices and seated within spinal anchors associated with the percutaneous access devices.
Figure 2A:
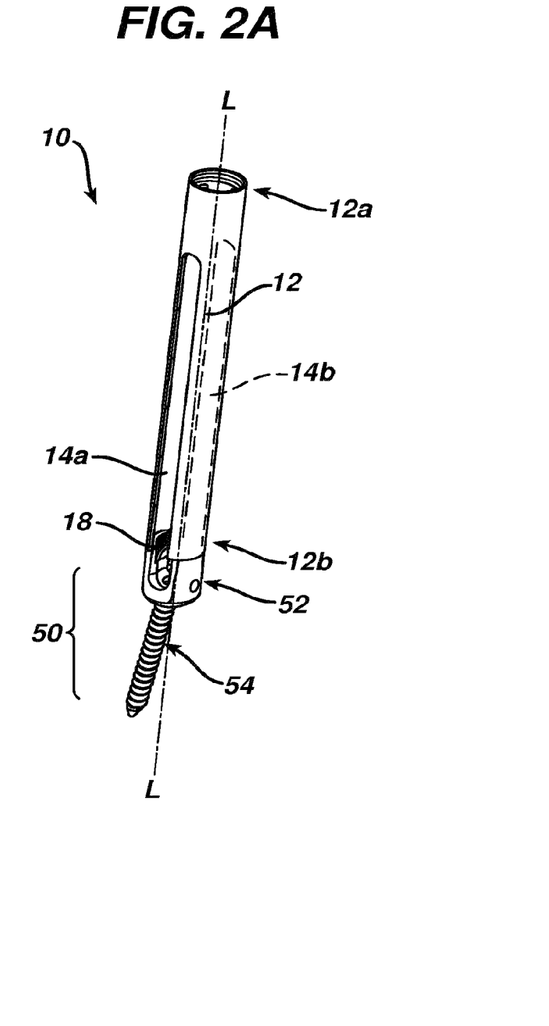
FIG. 2A is a perspective view of an exemplary embodiment of a percutaneous access device releasably engaged to a spinal anchor.
Figure 2B:
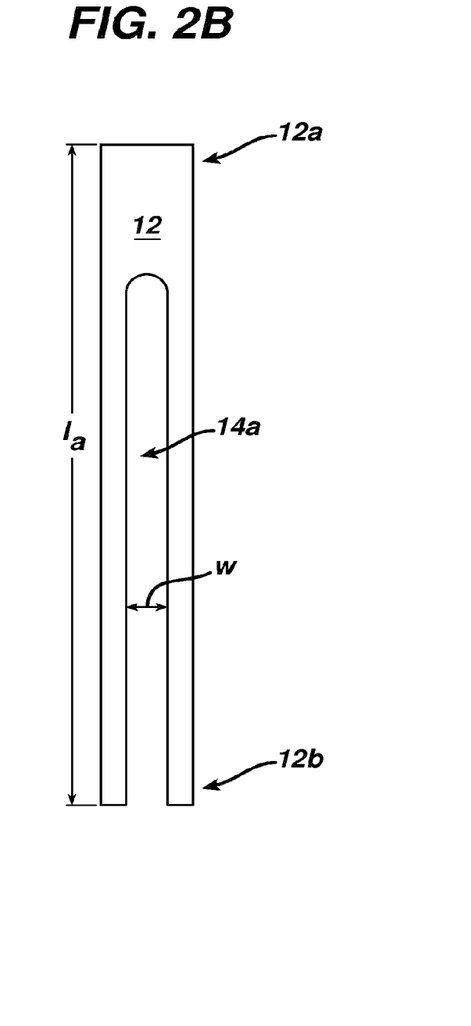
FIG. 2B is a side view of the percutaneous access device of FIG. 2A.

An exemplary embodiment of a method for delivering a spinal fixation element to the spine in a minimally invasive surgical technique is depicted in FIGS. 1A-1D. As shown in FIG. 1A, the method includes engaging a plurality of spinal implant assemblies 10a, 10b, 10c, 10d, 10e to a plurality of spinal locations 20a, 20b, 20c, 20d, 20e. While a variety of such assemblies can be used to perform the methods disclosed herein, FIGS. 2A and 2B illustrate an exemplary embodiment of such an assembly 10 which includes a percutaneous access device 12 mated to a spinal anchor 50 that is embedded in a vertebral body. As shown, the percutaneous access device 12 can be in the form of a generally elongate, cylindrical tube having a longitudinal axis L that extends between proximal and distal ends 12a, 12b. The size of the access device 12 can vary depending on the intended use. In certain exemplary embodiments, for example, the percutaneous access device 12 may have a length $l_a$ that allows the proximal end 12a of the access device 12 to be positioned outside the patient's body, while the distal end 12b of the access device 12 is coupled to, or positioned adjacent to, a spinal anchor 50 that is disposed in a vertebra in a patient's spine. The exemplary percutaneous access device 12 may be implanted through a minimally invasive percutaneous incision, which is a relatively small incision that typically has a length that is less than a diameter or width of the device 10 being inserted therethrough. For example, a minimally invasive percutaneous incision may be a stab or point incision through which the percutaneous access device 12 is positioned. As will be discussed, various embodiments of the method provided herein limit the number of incisions to the number of percutaneous access devices 12 required for the procedure.

The percutaneous access device 12 can further include opposed sidewall openings 14a, 14b (opening 14b is shown as dashed lines in FIG. 2A). As will be described, the opposed side wall openings 14a, 14b allow for a spinal fixation element 30 to pass laterally through the access device 12 thereby allowing for an optimized trajectory capable of facilitating the positioning of relatively longer fixation elements. In general, the width (W) of the sidewall openings 14a, 14b is generally sized in accordance with an outer diameter of the spinal fixation element 30. Also, the sidewall openings 14*a*, 14*b* typically begin at a location distal of the proximal end 12*a* of the access device 12 and extend to the distal end 12*b* of the device 12 thereby allowing the user to seat the fixation element 30 within the plurality of spinal anchors 50 (discussed below). As will be apparent to those skilled in the art, the opposed sidewall openings 14*a*, 14*b* can have virtually any shape, width, length, etc. capable of allowing passage therethrough of the spinal fixation element 30.

Referring to FIG. 2A, the percutaneous access device 12 can also be configured to releasably engage a spinal anchor 50. Thus, the distal end 12*b* of the percutaneous access device 12 can include one or more mating elements 18 formed thereon or therein for engaging the anchor 50. In an exemplary embodiment, the mating elements 18 are formed on opposed inner surfaces of the distal end 12*b* of the access device 12. As will be apparent to those skilled in the art, a wide range of such mating element can be utilized with the presently disclosed devices and methods. For example, the mating elements can include threads, a twist-lock engagement, a snap-on engagement, a dovetail coupling, or any other technique known in the art. In an exemplary embodiment, a percutaneous access device can be coupled to a corresponding bone anchor via a break-off coupling as disclosed in assignee's co-pending U.S. patent application Ser. No. 11/561,455, entitled "Break-off Screw Extensions," filed on Nov. 20, 2006, the entirety of which is incorporated herein by reference. Exemplary techniques for mating the percutaneous access device 12 to an anchor 50 are disclosed in commonly owned U.S. Pat. No. 7,179,261, entitled "Percutaneous Access Devices and Bone Anchor Assemblies," which is incorporated by reference in its entirety herewith. Those skilled in the art will appreciate that a variety of other techniques can be used to removably mate the percutaneous access device 12 to an anchor 50.

A variety of spinal anchors 50 can be used with the presently disclosed percutaneous access device(s) 12, including, for example, spinal screws, hooks, bolts, and wires. FIG. 2A illustrates a spinal screw that includes a distal, bone-engaging portion, e.g., a threaded shank 54, and a proximal, U-shaped receiver member head 52 that is adapted to seat a spinal fixation element 30, for example a fixation rod. The threaded shank 54 can be fixedly attached to the receiver head 52 to form a monoaxial screw, or alternatively the shank 54 can be configured as a polyaxial screw, as shown, that is rotatably disposed through an opening formed in the distal end of the receiver head 52 to allow rotation of the shank 54 with respect to the receiver head 52. A variety of techniques can be used to allow rotation of the head 52 with respect to the shank 54.

As indicated above, the method can include delivering any number of spinal implant assemblies 10*a*, 10*b*, 10*c*, etc. to a corresponding number of spinal locations 20*a*, 20*b*, 20*c*, etc. (e.g., vertebrae) as required by a given procedure. For example, the method can include delivering two assemblies 10*a*, 10*b*, three assemblies 10*a*, 10*b*, 10*c*, four assemblies 10*a*, 10*b*, 10*c*, 10*d*, etc. In the exemplary embodiment of FIG. 1A, the method includes engaging five assemblies 10*a*, 10*b*, 10*c*, 10*d*, 10*e* (i.e., spinal anchor 50 and associated percutaneous access device 12) to five respective spinal locations 20*a*, 20*b*, 20*c*, 20*d*, 20*e* thereby allowing for a four-level spinal fusion.

Following placement of the various assemblies 10*a*, 10*b*, 10*c*, etc., a spinal fixation element 30 can be delivered to the surgical site along an optimized trajectory and manipulated so as to seat the element 30 within the plurality of spinal anchors 50. The spinal fixation element 50 can be delivered through the same incision that accommodates one of the access devices 12, such as the most cephalad or caudal access device. FIGS. 1B-1D illustrate delivery of the spinal fixation element 30 from its point of insertion along a trajectory which facilitates positioning of a large-scale (e.g., greater than about 95 mm in length) spinal fixation element 30. More specifically, FIG. 1B shows the plurality of percutaneous access devices 12 engaged to a plurality of spinal locations 20*a*, 20*b*, etc. wherein each access device 12 is delivered via an individual incision and associated pathway. Once these devices 12 are so positioned, a distal portion 30*a* of the spinal fixation element 30 can be positioned adjacent an outer portion of a first percutaneous access device 12 and subsequently inserted through the corresponding first incision and delivered to a position adjacent to the distal end 12*b* of the percutaneous access device 12 as shown in FIG. 1B. Thus, the spinal fixation element 30 is delivered through the tissue via the same incision created for the delivery of the first percutaneous access device 12 thereby eliminating the need to create additional incision(s) to accommodate the fixation element. The spinal fixation element 30 can be delivered at any angle capable of facilitating delivery and placement of the element 30 relative to the plurality of access device(s) 12. For example, the spinal fixation element 30 can be delivered substantially parallel to a longitudinal axis (L) of the percutaneous access device 12. In other embodiments, the spinal fixation element 30 can be delivered at an angle of about 45° or less relative to the longitudinal axis (L) of the percutaneous access device 12.

Referring to FIG. 1C, the fixation element 30 can be further be manipulated so as to insert the distal end 30*a* of the element 30 laterally through the opposed sidewall openings 14*a*, 14*b* of the first percutaneous access device 30. Once the fixation element 30 has passed through the sidewall openings 14*a*, 14*b* of the first percutaneous access device 12, the element 30 is further advanced through the opposed sidewall openings of all additional percutaneous access devices 12 of the remaining assemblies 10*b*, 10*c*, 10*d*, 10*e*. Finally, as shown in FIG. 1D, the spinal fixation element 30 is positioned through the opposed sidewall openings 14*a*, 14*b* of each percutaneous access device 12 and placed within the plurality of spinal anchors 50 disposed within the various spinal locations 20*a*, 20*b*, 20*c*, 20*d*, 20*e* such that at least a portion of the spinal fixation element resides within each of the plurality of spinal anchors 50. Following this placing step, the spinal fixation element 30 can then be detached from a manipulation instrument 40 (discussed below) and the instrument 40 can be withdrawn from the treatment site. The ability to securely engage the fixation element 30 during placement and positioning of the element 30 within the plurality of bone anchors 50 in contrast to releasing the fixation element 30 and attempting to manually (or by means of additional devices) position the element 30 can significantly improve the efficiency and effectiveness of the stabilization procedure. The method can further include a mechanism for securing the spinal fixation element 30 to the plurality of spinal anchors 50, for example, by threading a plurality of set screws (not shown) into the plurality of spinal anchors 50.

In light of the above-described delivery trajectory, the percutaneous access devices 12 can include closed proximal ends 12*a* thereby providing various advantages. For example, closed end devices are easier to manipulate and/or engage additional instrumentation thereto as compared to open-ended devices. Further, the use of such closed proximal end devices 12*a* allows for a single percutaneous access device 12 to be employed as compared to common procedures requiring both closed and open ended devices wherein the use of a single type of access device 12 facilitates the user's ability to determine the depth of the access device 12 relative to the tissue and also facilitates the user's ability to determine if any of the devices are misaligned. For at least these reasons, the use of percutaneous access devices 12 having closed proximal ends 12a provides significant advantages over commonly known techniques and devices.

As indicated above, the spinal fixation element 30 can include virtually any element capable of providing the desired spinal fixation. For example, the spinal fixation element 30 can be a rigid rod (e.g., a titanium rod), a polymer rod, and/or a dynamic element. In some embodiments, the fixation element can include a variable diameter along a length of the element. Additionally, the length and/or dimensions of the fixation element can be selected and/or configured as required by a given procedure. For example, in an exemplary embodiment, the spinal fixation element 30 can have a length greater than about 95 mm. In other embodiments, the spinal fixation element 30 can have a length greater than about 100 mm, greater than about 105 mm, greater than about 110 mm, greater than about 120 mm, etc. It will be apparent to those skilled in the art that a spinal fixation element 30 can have any length as required by a given procedure. For example, the fixation element can have a length suitable for a 2-level procedure (i.e., a single construct), 3-level procedure, a 4-level procedure, a 5-level procedure, or greater level procedure. Additionally, the spinal fixation element can be straight, pre-contoured to match the desired curvature of the spine in the appropriate region, or bendable by a surgeon to achieve a desired contour.

Figure 3A:
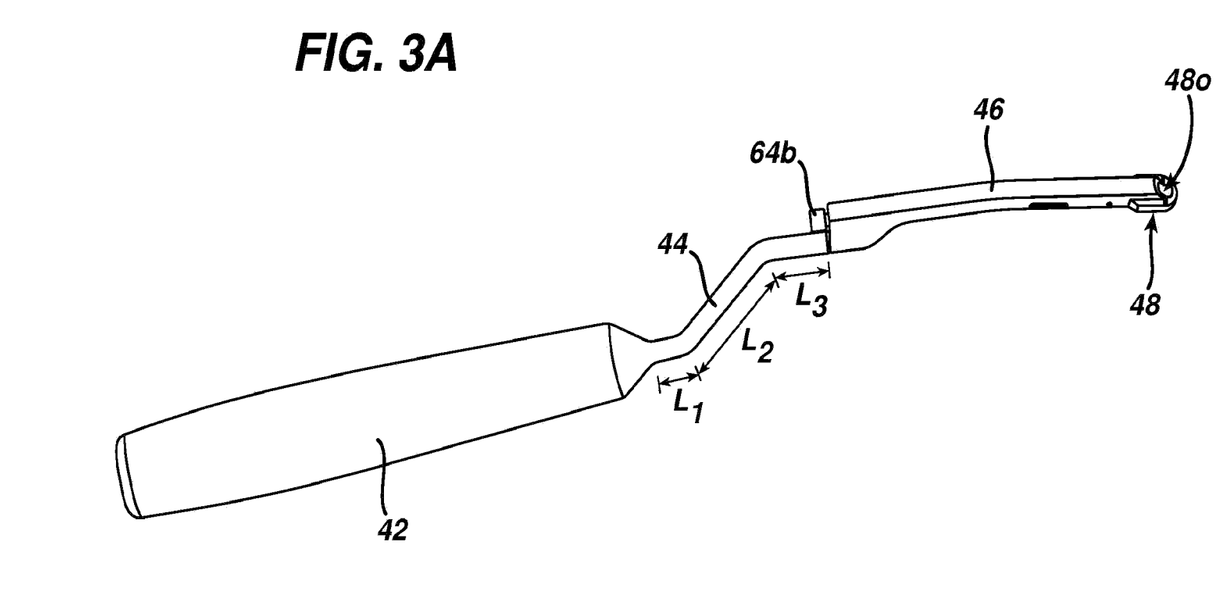
FIG. 3A is a perspective view of an exemplary embodiment of a manipulation instrument.
Figure 3B:
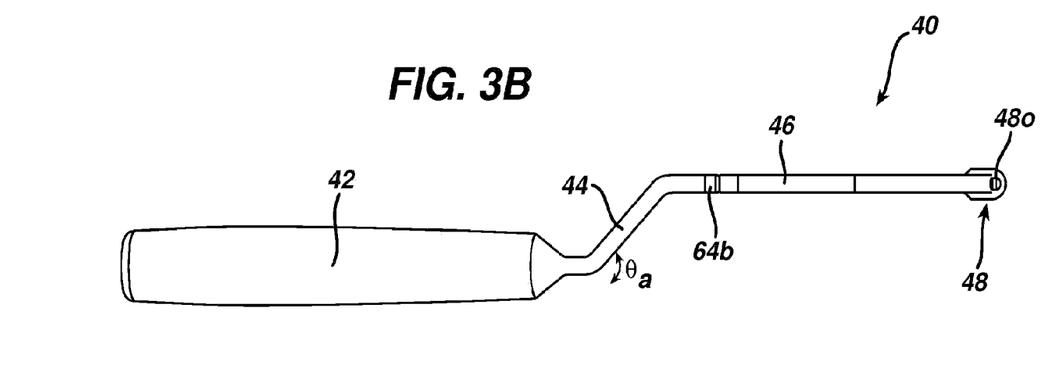
FIG. 3B is a side view of the manipulation instrument of FIG. 3A.
Figure 3C:
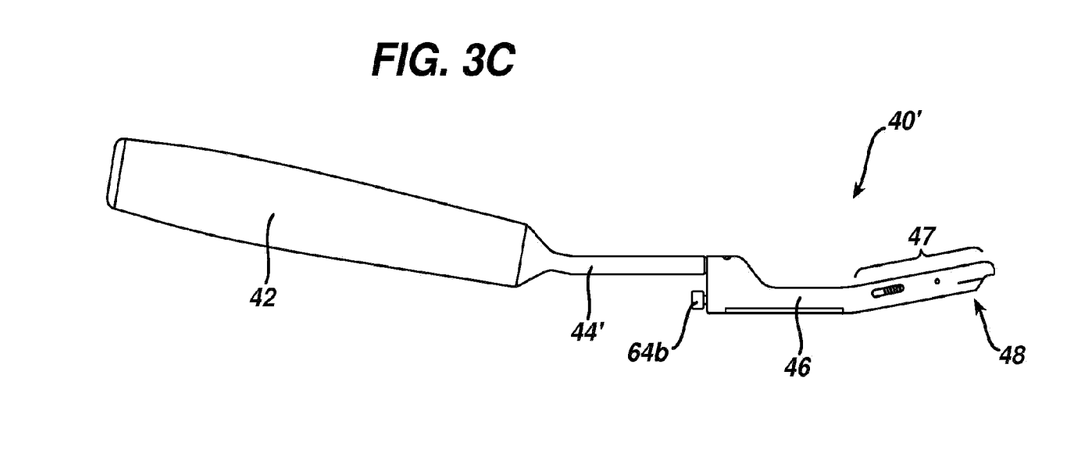
FIG. 3C is a top view of another embodiment of a manipulation instrument.

In addition to the methods provided above, various embodiments of a manipulation instrument 40 configured to facilitate positioning and/or manipulation of the element 30 are also provided herein. As described below, the manipulation instrument 40 can be configured in various manners to facilitate delivery of a large-scale fixation element 30 as well as proper positioning of the element within the various spinal anchors. Such a manipulation instrument, as well as other components described herein, can be provided as part of a kit or system. FIGS. 3A-3C provide various views of an exemplary embodiment of a manipulation instrument 40 capable of releasably engaging and delivering a spinal fixation element 30 to a desired surgical site. As shown, the instrument 40 can include a shaft 44 having a proximal end coupled to a handle 42 and a distal end coupled to a clamping mechanism 46. In order to facilitate manipulation of large-scale fixation elements 30, the shaft 44 of the instrument 40 can be offset relative to the handle 42 such that the handle 42 is not collinear with the clamping mechanism 46 thereby positioning the handle 42 away from the patient which enhances maneuverability and/or visibility as the user manipulates the spinal fixation element 30 into a desired position (see FIG. 1C). Such an offset configuration can be achieved in various ways. For example, as shown in FIG. 3A the shaft 44 can include a first length $L_1$, a second length $L_2$ and a third length $L_3$ wherein the second length $L_2$ is oriented at an angle $\theta_a$ relative to the first length $L_1$. Also, as will be further described below, the above-described configuration of the instrument 40 (e.g., the offset and various curves) can allow for easier access to an actuator 64b configured to release a spinal fixation element engaged to the instrument 40. Additionally, the distal portion of the clamping mechanism 46 can be configured to be at an angle $\theta_b$ relative to the proximal end of the clamping mechanism 46 thereby ensuring proper positioning of the fixation element 30 within the spinal anchors. More specifically, angling the clamping mechanism 46 as such ensures that the fixation element is completely positioned within the first bone anchor as opposed to over-insertion of the element 30 which could prevent a closure mechanism from properly securing the fixation element 30 within the first bone anchor.

The handle 42 of the instrument 40 can also be configured to provide enhanced maneuverability and/or control over the fixation element during delivery to the surgical site. For example, the handle 42 can be oversized (e.g., large diameter and/or length) so as to provide leverage to a user relative to the fixation element. Such added leverage and enhanced control can be of increased importance for those procedures requiring the use of large fixation elements. Additionally, as illustrated in FIG. 3C, the handle 42 can be angled relative to the shaft thereby facilitating delivery of the fixation element. As will be appreciated by those skilled in the art, the handle can be configured in various other manners so as to improve the user's ability to accurately deliver and/or position the fixation element.

Figure 4A:
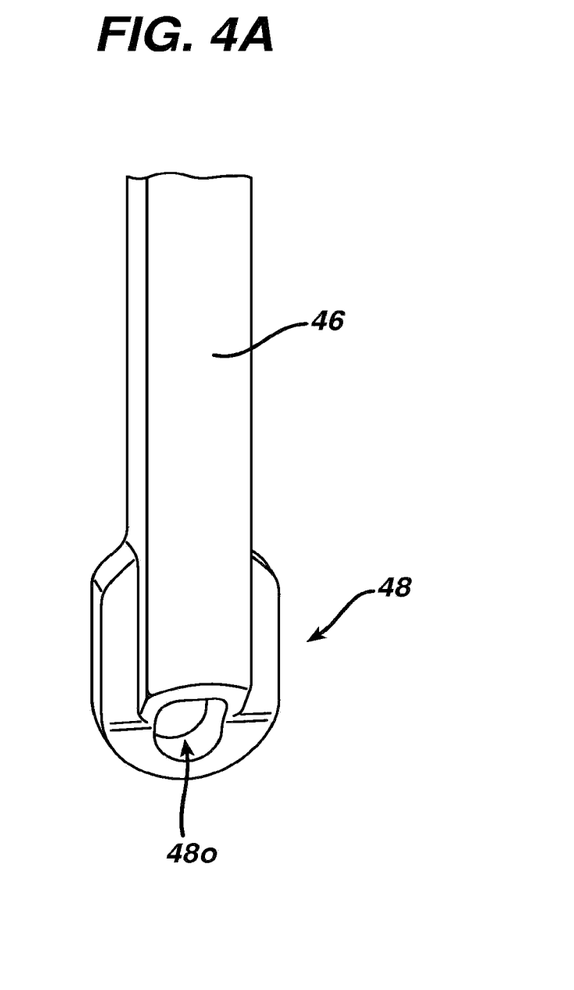
FIG. 4A is a view of a distal end of the manipulation instrument of FIG. 3A.
Figure 4B:
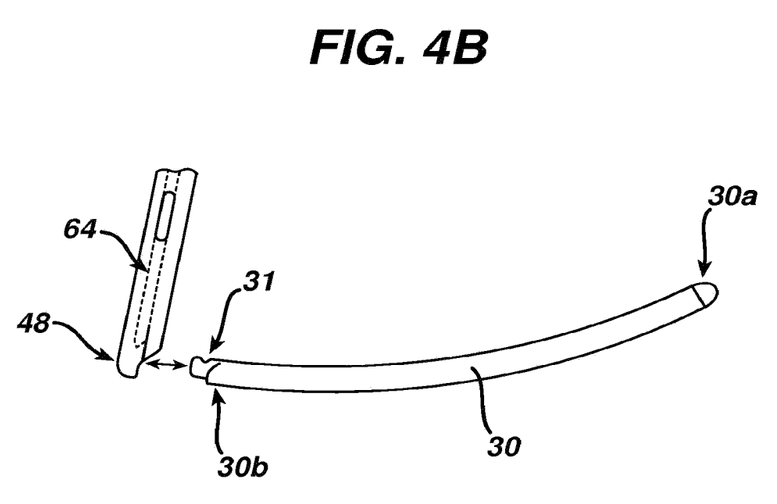
FIG. 4B is a representation of an orientation between a proximal portion of a spinal fixation element and the distal end of the manipulation instrument of FIG. 4A prior to engagement.
Figure 5:
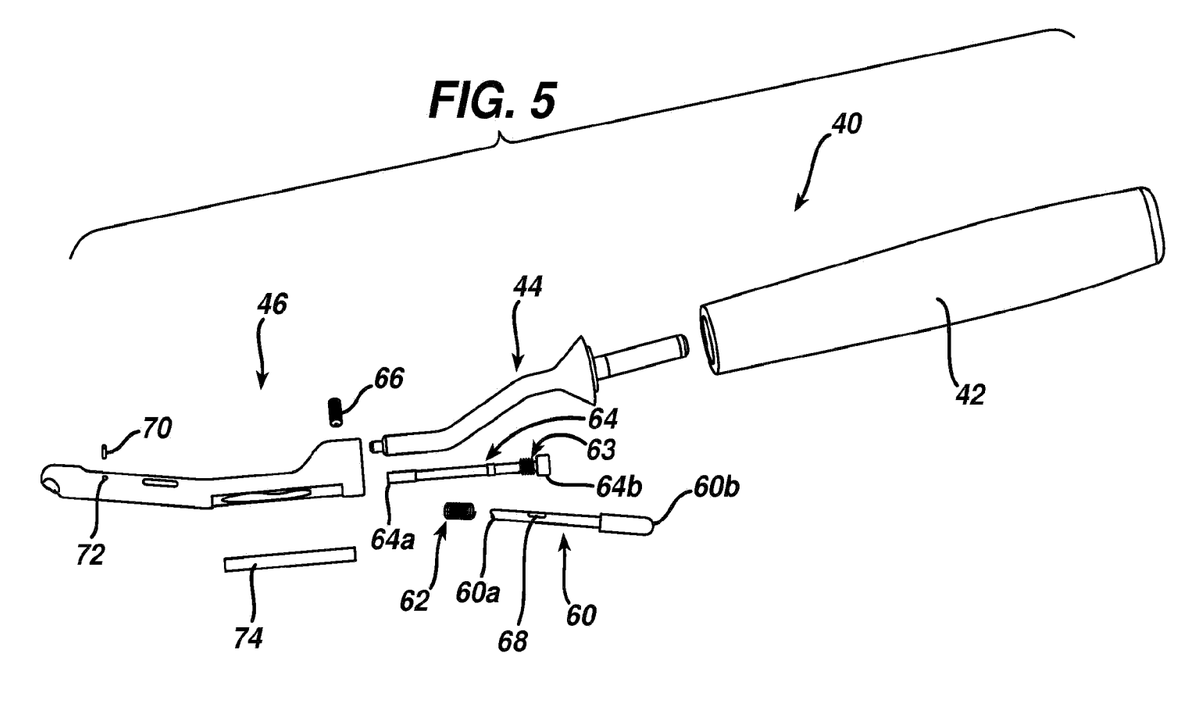
FIG. 5 is an exploded view of the manipulation instrument of FIG. 3A.

As indicated above, the instrument 40 can include a clamping mechanism 46 having a distal portion 48 configured to releasably engage the spinal fixation element 30. For example, as shown in FIGS. 4A and 4B, the distal portion 48 of the clamping mechanism 46 can include an opening 48o configured to receive the proximal end 30a of the spinal fixation element 30. When the proximal end 30a of the fixation element 30 is positioned within the opening 48o, the element 30 can be secured therein by various mechanisms. For example, as will be explained in greater detail in relation to FIG. 5, the clamping mechanism 46 can be in communication with an actuator 64b configured to allow a user to selectively engage or disengage the fixation element 30. FIG. 5 provides an exploded view of the manipulation instrument 40 to illustrate the inner workings of the clamping mechanism 46. As shown, the instrument 40 is comprised of various components such as the clamping mechanism 46, the shaft 44, and the handle 42. In such an embodiment, the various components can be coupled to one another via any well known method (e.g., use of a ball plunger 66). In other embodiments, any or all of these components 42, 44, 46 can be permanently mated to one another or can be formed as a single component. Referring to the clamping mechanism 46, a distal portion 47 (see FIG. 3B) of the mechanism 46 can be angled ($\theta_b$) so as to ensure proper positioning of the fixation element 30 within the bone anchors. Additionally, the clamping mechanism 46 can include a central bore (not shown) extending therethrough and in communication with the distal opening 48o thereby allowing an engagement element 60 and a driver 64 to slide along the central bore so as to engage and/or disengage the fixation element 30. As will be described, these elements 60, 64 can be configured to slide along the central bore in response to a force supplied to the actuator 64b. In this example, the elements 60, 64 will be shown as distinct elements. However, as will be clear to those skilled in the art, these components could be a single element or more than two elements.

Thus, in the exemplary embodiment shown in FIG. 5, the engagement element 60 can include a distal end 60a configured to securely engage the proximal portion 30b of the fixation element 30. As illustrated in FIG. 4B, in a biased state, the distal portion 60a of the engagement element 60 resides in a retracted position within the clamping mechanism 46. Upon actuation (described below), the distal portion 60a is advanced distally so as to engage a corresponding groove 31 (FIG. 4B) of the fixation element 30. The engagement element 60 further includes a proximal end 60b configured to have a larger diameter as compared to the remainder of the element 60 thereby allowing a resilient element (e.g., a spring) 62 to be positioned over the element 60 and sized to abut the enlarged distal portion 60b. When assembled, a distal portion of the spring 62 can engage the surrounding walls of the inner bore thereby resulting in the above-described biased, retracted position. As will be shown below, in use, the user can supply a force to the actuator 64b which results in the spring 62 being compressed and the distal end 60a of the engagement element 60 being brought into contact with the portion of fixation element 30 disposed within the distal opening 480. Additionally, a slot 68 can be incorporated within the engagement component 60 such that the slot 68 is configured to receive a set-pin 70 disposed through a hole 72 in the distal portion of the clamping mechanism 46. Thus, the set-pin 70 and the associated slot 68 can be configured to limit movement of the engagement element 60 between the biased, retracted position and the extended position.

As mentioned, in this exemplary embodiment, a driver 64 can be in communication with the engagement element 60 such that the driver 64 can translate a force from the actuator 64b to the engagement element 60. Thus, as shown, the driver 64 can include a distal end 64a configured to abut the proximal end 60b of the engagement element 60, and the driver 64 can further include the actuator 64b at the proximal end and accessible to a user. A proximal portion of the driver 64 (distal of the actuator 64b) can include a threaded portion 63 configured to engage a corresponding threaded portion (not shown) incorporated into the clamping mechanism 46. Thus, by rotating the actuator 64b in a first direction (e.g., clockwise), the driver 64 can advance in a distal direction via the threaded portions. As the driver 64 advances, a force is supplied to the engagement element 60 thereby overcoming the biasing force of the spring 62 and forcing the distal end 60a of the engagement element 60 against the proximal end 30b of the spinal fixation element 30. Upon rotating the actuator 64b in an opposite direction (e.g., counter clockwise), the force is removed and the engagement element 60 is free to return to the biased, retracted position. Referring once again to FIG. 5, the clamping mechanism 46 can also include a removable portion 74 thereby allowing for maintenance, cleaning, and/or repair/replacement of any of the various internal components. In other embodiments, the portion 74 is welded in position.

Figure 6:
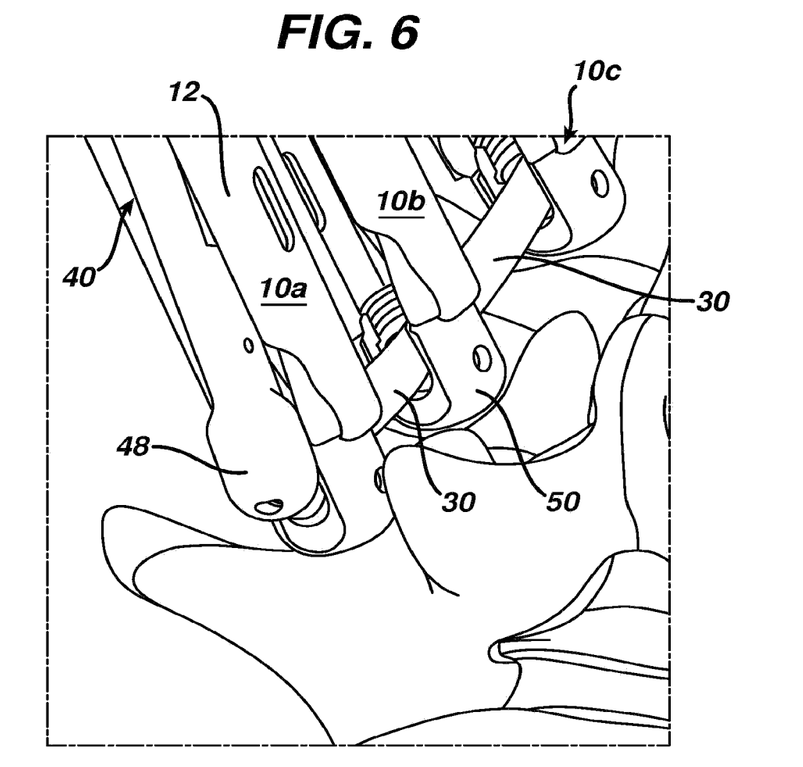
FIG. 6 is a view of the distal end of the manipulation instrument engaged to the spinal fixation element wherein the distal end of the instrument is configured as a stop element.

In another embodiment, the manipulator instrument 40 can be configured to facilitate proper positioning of the spinal fixation element 30 relative to the plurality of percutaneous access devices 12 and corresponding spinal anchors 50. For example, as illustrated in FIG. 6, a distal end 48 of the clamping mechanism 46 can be configured to prevent passage of the distal portion 48 within and/or through the sidewall opening of the first percutaneous access device 12 thereby indicating to the user when the spinal fixation element 30 has been delivered through each of the assemblies 10a, 10b, etc. utilized by the given procedure. The distal end 48 of the extension can include various configurations capable of achieving the desired result. In an exemplary embodiment, the distal portion 48 of the clamping mechanism 46 can be substantially planar and has a diameter larger than that of the spinal fixation element 30. Those skilled in the art will appreciate that the distal end 48 can include virtually any such configuration capable of preventing passage of the distal end 48 of the clamping mechanism 46 within and/or through the opposed sidewall openings.

One skilled in the art will appreciate further features and advantages of the presently disclosed methods and/or devices based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A method for delivering a spinal fixation element to a surgical site, comprising:
   engaging a plurality of percutaneous access devices to a corresponding number of spinal locations, each access device being delivered to the respective spinal location via a respective incision such that at least a first access device is delivered via a first incision, each percutaneous access device extending along a longitudinal axis between a distal end disposed adjacent to a spinal anchor and a proximal end positioned outside a patient's body;
   releasably engaging a proximal end of a spinal fixation element to a manipulation instrument;
   delivering a distal portion of the spinal fixation element through the first incision in an orientation substantially parallel to the longitudinal axis of the first percutaneous access device;
   manipulating the distal portion of the spinal fixation element through opposed distal sidewall openings of the first percutaneous access device;
   guiding the distal portion of the spinal fixation element through opposed distal sidewall openings of each remaining percutaneous access device;
   placing the spinal fixation element within the plurality of spinal anchors such that at least a portion of the spinal fixation element resides within each of the plurality of spinal anchors, the spinal fixation element maintaining a fixed orientation relative to a handle of the manipulation instrument during the delivering, manipulating, guiding, and placing steps; and
   releasing the spinal fixation element from the manipulation instrument following the placing step.

2. The method of claim 1, wherein the spinal fixation element is a rod.

3. The method of claim 1, wherein the spinal fixation element has a length configured to provide a three-level spinal fixation.

4. The method of claim 1, wherein the spinal fixation element has a length configured to provide at least a four-level spinal fixation.

5. The method of claim 1, wherein three percutaneous access devices are utilized.

6. The method of claim 1, wherein at least four percutaneous access devices are utilized.

7. The method of claim 1, wherein the proximal end of at least one percutaneous access device is closed.

8. The method of claim 1, wherein the proximal end of at least one percutaneous access device is open.

9. The method of claim 1, wherein the releasably engaging step comprises:
   disposing the proximal end of the spinal fixation element within an opening formed in a distal portion of the manipulation instrument; and
   securing the spinal fixation element to the manipulation instrument by engaging a distal end of an engagement element to a notch formed in a proximal portion of the spinal fixation element, the engagement element being disposed within a distal portion of the manipulation instrument.

10. The method of claim 9, wherein the releasing step comprises:
    applying an actuation force to an actuator coupled to the manipulation instrument wherein the actuation force disengages the distal end of the engagement element from the notch formed in the proximal portion of spinal fixation element.

11. A minimally invasive method for delivering a spinal fixation element to a surgical site, comprising:
   inserting a plurality of access devices into a body through a percutaneous incision for each access device such that a proximal end of each access device is positioned outside the body and a distal end engages a spinal anchor disposed in a vertebra;
   engaging a proximal portion of a spinal fixation element to a distal portion of a manipulation instrument;
   inserting the spinal fixation element through one of the percutaneous incisions for one of the access devices with a distal portion of the spinal fixation element positioned outside of an outer portion of a first percutaneous access device during insertion, and wherein the spinal fixation element is inserted in an orientation substantially parallel to a longitudinal axis of the access device;
   after inserting the spinal fixation element through one of the percutaneous access incisions, manipulating the spinal fixation element such that the spinal fixation element passes through opposed sidewall openings of each percutaneous access device;
   placing the spinal fixation element in the plurality of spinal anchors such that at least a portion of the spinal fixation element resides within each bone anchor, the spinal fixation element maintaining a fixed orientation relative to a handle of the manipulation instrument during the inserting, manipulating, and placing steps; and
   disengaging the spinal fixation element from the manipulation instrument following the placing step.

12. The method of claim 11, wherein the spinal fixation element is a rod.

13. The method of claim 11, wherein the spinal fixation element has a length configured to provide a three-level spinal fixation.

14. The method of claim 11, wherein the spinal fixation element has a length configured to provide at least a four-level spinal fixation.

15. The method of claim 11, wherein the engaging step comprises:
   disposing the proximal end of the spinal fixation element within an opening formed in a distal portion of the manipulation instrument; and
   securing the spinal fixation element to the manipulation instrument by engaging a distal end of an engagement element to a notch formed in a proximal portion of the spinal fixation element, the engagement element being disposed within a distal portion of the manipulation instrument.

16. The method of claim 15, wherein the releasing step comprises:
   applying an actuation force to an actuator coupled to the manipulation instrument wherein the actuation force disengages the distal end of the engagement element from the notch formed in the proximal portion of spinal fixation element.

17. A method for delivering a spinal fixation element to a surgical site, comprising:
   engaging a plurality of percutaneous access devices to a corresponding number of spinal locations, each access device being delivered to the respective spinal location via a respective incision such that at least a first access device is delivered via a first incision, each percutaneous access device extending along a longitudinal axis between a distal end disposed adjacent to a spinal anchor and a proximal end positioned outside a patient's body;
   releasably engaging a proximal portion of a spinal fixation element to a distal portion of a manipulation instrument, the manipulation instrument having a handle portion coupled to an elongate shaft via an offset;
   delivering a distal portion of the spinal fixation element through the first incision in an orientation substantially parallel to the longitudinal axis of the first percutaneous axis device;
   manipulating the distal portion of the spinal fixation element through opposed sidewall openings of the first percutaneous access device;
   guiding the distal portion of the spinal fixation element through opposed sidewall openings of each remaining percutaneous access device with the distal portion of the manipulation instrument being prevented from passing through any of the opposed sidewall openings;
   placing the spinal fixation element within the plurality of spinal anchors such that at least a portion of the spinal fixation element resides within the spinal anchors, the spinal fixation element maintaining a fixed orientation relative to the handle portion of the manipulation instrument during the delivering, manipulating, guiding, and placing steps; and
   releasing the spinal fixation element from the manipulation instrument following the above placing step.

18. The method of claim 17, wherein a distal portion of the elongate shaft is angled relative to a proximal portion of the elongate shaft.

19. The method of claim 17, further comprising:
   contacting a distal end of the manipulation instrument to a distal portion of a first percutaneous access device, the distal end of the manipulation instrument configured to prevent passage of the instrument through the opposed side-wall openings, the contacting step performed prior to the releasing step.

* * * * *